United States Patent
Zhou

(10) Patent No.: US 11,826,400 B2
(45) Date of Patent: *Nov. 28, 2023

(54) NEUREGULIN BASED COMPOSITIONS AND USES THEREOF FOR PREVENTING, TREATING OR DELAYING THE MYOCARDIAL ISCHEMIA-REPERFUSION INJURY

(75) Inventor: Mingdong Zhou, Shanghai (CN)

(73) Assignee: ZENSUN (SHANGHAI) SCIENCE & TECHNOLOGY LIMITED, Shanghai (CN)

( * ) Notice: Subject to any disclaimer, the term of this patent is extended or adjusted under 35 U.S.C. 154(b) by 94 days.

This patent is subject to a terminal disclaimer.

(21) Appl. No.: 13/575,932

(22) PCT Filed: Jan. 11, 2011

(86) PCT No.: PCT/CN2011/070178
§ 371 (c)(1),
(2), (4) Date: Jul. 27, 2012

(87) PCT Pub. No.: WO2011/091723
PCT Pub. Date: Aug. 4, 2011

(65) Prior Publication Data
US 2013/0078235 A1 Mar. 28, 2013

(30) Foreign Application Priority Data
Jan. 29, 2010 (CN) .......................... 201010112974.0

(51) Int. Cl.
| A61K 38/18 | (2006.01) |
| A61K 45/06 | (2006.01) |
| A61P 9/10 | (2006.01) |
| A61P 37/06 | (2006.01) |
| A61P 39/06 | (2006.01) |

(52) U.S. Cl.
CPC .......... *A61K 38/1808* (2013.01); *A61K 38/18* (2013.01); *A61K 45/06* (2013.01)

(58) Field of Classification Search
CPC ................ A61K 38/18; A61K 38/1808; A61K 2300/00; A61K 45/00
USPC .............................. 424/133.1, 94.4; 514/9.6
See application file for complete search history.

(56) References Cited

U.S. PATENT DOCUMENTS

| 5,530,109 A | 6/1996 | Goodearl et al. |
| 5,716,930 A | 2/1998 | Goodearl et al. |
| 5,834,229 A | 11/1998 | Vandlen et al. |
| 7,226,907 B1 | 6/2007 | Zhou |
| 7,612,164 B2 | 11/2009 | Zhou |
| 7,795,212 B2 | 9/2010 | Zhou |
| 7,964,555 B2 | 6/2011 | Zhou |
| 8,476,405 B2 | 7/2013 | Zhou |
| 8,609,620 B2 | 12/2013 | Zhou |
| 8,785,387 B2 | 7/2014 | Zhou |
| 9,434,777 B2 | 9/2016 | Zhou |
| 9,555,076 B2 | 1/2017 | Zhou |
| 9,580,515 B2 | 2/2017 | Zhou |
| 9,655,949 B2 | 5/2017 | Zhou |
| 2006/0199767 A1 | 9/2006 | Zhou |
| 2007/0129296 A1 | 6/2007 | Zhou |
| 2007/0190127 A1 | 8/2007 | Zhou |
| 2007/0213264 A1 | 9/2007 | Zhou |
| 2009/0156488 A1 | 6/2009 | Zhou |
| 2010/0143317 A1* | 6/2010 | Pecora ................. A61K 31/155 424/93.72 |
| 2011/0229444 A1 | 9/2011 | Zhou |
| 2013/0079281 A1 | 3/2013 | Zhou |
| 2014/0031284 A1 | 1/2014 | Zhou |
| 2014/0135265 A1 | 5/2014 | Zhou |
| 2016/0089329 A1 | 3/2016 | Zhou |
| 2016/0095903 A1 | 4/2016 | Zhou |
| 2016/0297859 A1 | 10/2016 | Zhou |
| 2017/0007671 A1 | 1/2017 | Zhou |

(Continued)

FOREIGN PATENT DOCUMENTS

| CN | 1498656 A | 5/2004 |
| CN | 1768859 A | 5/2006 |

(Continued)

OTHER PUBLICATIONS

Takemura, Nihon Kyobu Geka Gakkai, pp. 247-253, 1993 (Abstract Only).*
Guo et al., Brain Res., vol. 1087, pp. 180-185, 2006.*
Shyu et al., Neurobio. Aging, vol. 25, pp. 935-944, 2004.*
Ramachandran et al (Vet Pathol 45: 698-706, 2008).*
Pentassuglia et al (Exp Cell Res 315: 627-637, 2009).*
Fang et al (Chin Med J 123: 3597-3604, Dec. 2010).*
Yellon et al (N Engl J Med 357: 1121-1135, 2007).*

(Continued)

*Primary Examiner* — Daniel E Kolker
*Assistant Examiner* — Aditi Dutt
(74) *Attorney, Agent, or Firm* — Jones Day

(57) ABSTRACT

The present invention elates to the applications of neuregulin in the preparation of drugs for preventing, treating or delaying the ischemia-reperfusion injury (IRI) in mammals, particularly in humans. In particular, the present invention provides the neuregulin based compositions and methods for preventing, treating or delaying the myocardial ischemia-reperfusion injury. Specifically, although it has been shown in cytological experiments, animal studies and clinical trials that neuregulin can improve the cytoskeleton structure of myocytes and cardiac function, it is still unknown whether neuregulin has effects on the myocardial ischemia-reperfusion injury. The present invention proves that neuregulin reduces the infarction size in the rat IRI model, which indicates that neuregulin can be used for preventing, treating or delaying the myocardial ischemia-reperfusion injury.

20 Claims, 1 Drawing Sheet
Specification includes a Sequence Listing.

(56) References Cited

U.S. PATENT DOCUMENTS

| | | | |
|---|---|---|---|
| 2017/0232068 A1 | 8/2017 | Zhou |
| 2017/0313784 A1 | 11/2017 | Zhou |
| 2017/0360889 A1 | 12/2017 | Zhou |

FOREIGN PATENT DOCUMENTS

| | | |
|---|---|---|
| CN | 1836731 A | 9/2006 |
| CN | 101007027 A | 8/2007 |
| WO | WO 97/09425 | 3/1997 |
| WO | WO 00/37095 | 6/2000 |
| WO | WO 00/64400 | 11/2000 |
| WO | WO03/099300 | 12/2003 |
| WO | WO 03/099320 A1 | 12/2003 |
| WO | WO 2003/099320 | 12/2003 |
| WO | WO 2003/099321 | 12/2003 |
| WO | WO 2006/128125 A2 | 11/2006 |
| WO | WO 2007/062594 | 6/2007 |
| WO | WO 2007/076701 | 7/2007 |
| WO | WO 2008/028405 A1 | 3/2008 |
| WO | WO 09/033373 A1 | 3/2009 |
| WO | WO 2009/033373 | 3/2009 |
| WO | WO 2010/060265 | 6/2010 |
| WO | WO 2010/060266 | 6/2010 |
| WO | WO 2010/142141 | 12/2010 |
| WO | WO 2011/091723 | 8/2011 |
| WO | WO 2013/053076 | 4/2013 |
| WO | WO 2013/053158 | 4/2013 |
| WO | WO2014/187342 | 11/2014 |
| WO | WO 2015/101182 A1 | 7/2015 |
| WO | WO2016/058493 A1 | 4/2016 |

OTHER PUBLICATIONS

Altiok et al., "ErbB3 and ErbB2/neu mediate the effect of heregulin on acetylcholine receptor gene expression in muscle: differential expression at the endplate," *EMBO J.*, 14(17):4258-4266 (1995).

Carraway et al., "Neuregulin-2, a new ligand of ErbB3/ErbB4-receptor tryrosine kinases," *Nature*, 387:512-517 (1997).

Chang et al., "Ligands for ErbB-family receptors encoded by a neuregulin-like gene," *Nature*, 387:509-512 (1997).

Culouscou et al., "HER4 receptor activation and phosphorylation of Shc proteins by recombinant heregulin-Fc fusion proteins," *J. Biol. Chem.*, 270(21):12857-12863 (1995).

EST Profile—Rn. 10228, :Erbb3: V-erb-b2 erythroblastic leukemia viral oncogene homolog 3 (avian), Retrieved on Feb. 10, 2015, [online], Retrieved from the internet :<http://www.ncbi.nlm.nih.gov/UniGene/ESTProfileViewer.cgi?uglist=Rn.10228>.

Higashiyama et al., "A novel brain-derived member of the epidermal growth factor family that interacts with ErbB3 and ErbB4," *J. Biochem.*, 122:675-680 (1997).

Hijazi et al., "NRG-3 in human breast cancers: activation of multiple erbB family proteins," *Int. J. Oncol.*, 13:1601-1607 (1998).

Holmes et al., Identification of heregulin, a specific activator of p185$^{erB2}$, *Science*, 256(5060):1205-1210 (1992).

Kuramochi et al., "Cardiac endothelial cells regulate reactive oxygen species-induced cardiomyocyte apoptosis through neuregulin-1β/erbB4 signaling," *J. Biol. Chem.*, 279(49):51141-51147 (2004).

Li et al., "Effects of neuregulin on expression of MMP-9 and NSE in brain of ischemia/reperfuison rat," *J. Mol. Neurosci.*, 38:207-215 (2009).

Li et al., "Neuregulin attenuated cerebral ischemia-Creperfusion injury via inhibiting apoptosis and upregulating aquaporin-4," *Neurosci. Lett.*, 443(3):155-159 (2008).

Lin et al., "Neuregulin-1 reduces ischemia-reduced brain damage in rats," *Abstracts Annual Meeting Society for Neuroscience*, Society For Neuroscience, Washington, D.C., Presentation No. 883.10 (2003).

Liu et al., "Neuregulin-1/erbB-activation improves cardiac function and survival in models of ischemic, dilated, and viral cardiomyopathy," *J. Am. Coll. Cardio.*, 48(7):1438-1447 (2006).

Sadick et al., "Analysis of heregulin-induced ErbB2 phosphorylation with a high-throughput kinase receptor activation enzyme-linked immunosorbant assay," *Analytical Biochem.*, 235:207-214 (1996).

Shyu et al., "Neuregulin-1 reduces ischemia-induced brain damage in rats," *Neurobiology Aging*, 25:935-955 (2004).

Tao, "The interfering effect and probable mechanism of neuregulin-1β on cerebral ischemia reperfusion injury in mice," *Acta Anatomica Sinica*, 39(1):35-39 (2008), English abstact.

Zhao et al., "Neuregulins promote survival and growth of cardiac myocytes. Persistence of ErbB2 and ErbB4 expression in neonatal and adult ventricular myocytes," *J. Biol. Chem.*, 273(17):10261-10269 (1998).

Armiger et al., "Mitochondrial changes in dog myocardium induced by neutral lactate in vitro," Lab. Invest., 31(1):29-33 (1974).

Belzer et al., "Principles of solid-organ preservation by cold storage," Transplantation, 45(4):673-676 (1988).

Jahania et al., "Heart preservation for transplantation: principles and strategies," Ann. Thorac. Surg., 68:1983-1987 (1999).

Eum et al., "Necrosis and apoptosis: sequence of liver damage following reperfusion after 60 min ischemia in rats," Biochem. Biophys. Res. Comm., 358:500-505 (2007).

Sobey et al., "Allopurinol and amlodipine improve coronary vasodilatation after myocardial ischaemia and reperfusion in anaesthetized dogs," Br. J. Pharmacol., 108:342-347 (1993).

\* cited by examiner

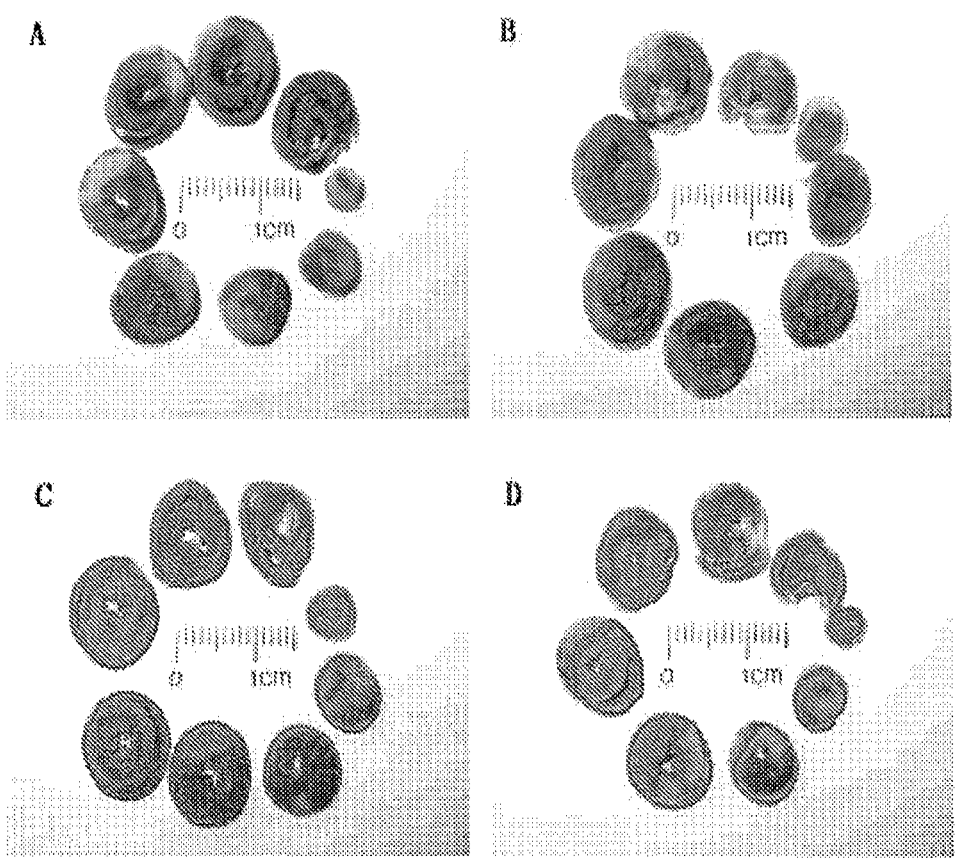

NEUREGULIN BASED COMPOSITIONS AND USES THEREOF FOR PREVENTING, TREATING OR DELAYING THE MYOCARDIAL ISCHEMIA-REPERFUSION INJURY

This application is a U.S. national stage application of PCT application serial No. PCT/CN2011/070178, filed Jan. 11, 2011, which claims priority to Chinese patent application No. 201010112974.0, filed Jan. 29, 2010, each of which is incorporated herein by reference in its entirety.

Incorporated herein by reference is the Sequence Listing being concurrently submitted via EFS-Web as an ASCII text file named 11748-035-999-seqlist.txt, created Jul. 27, 2012, and being 984 bytes in size.

FIELD OF THE INVENTION

The present invention relates to the use of neuregulin in the preparation of drugs for preventing, treating or delaying the ischemia-reperfusion injury in mammals, particularly in humans. In particular, the present invention provides the neuregulin based compositions and methods for preventing, treating or delaying the myocardial ischemia-reperfusion injury.

BACKGROUND OF THE INVENTION

Dredging the blood vessel or revascularization after ischemia, which was aimed at blood reperfusion, obtains favorable therapeutic effects in most instances, but under certain conditions it resulted in more serious consequences. Ischemia reperfusion injury (IRI) can be observed not only in clinic trials, but also proved by distinct species of animal studies, such as rabbit, rat, cavy, dog, swine and so on.

IRI has been the focus of cardiovascular research since the time when Jennings put forward the concept the first time in 1960. Early reperfusion may reduce the myocardial damage as sustained myocardial ischemia induces tissue damage and cell death, while plenty of animal studies and clinical observations revealed that blood reperfusion to the ischemic tissues may cause the myocardial ischemia damage more serious including arrhythmia, increased infarction size and enduring low ventricular systolic function. IRI is biochemically characterized by a depletion of oxygen during an ischemic event, a resultant increase in intracellular calcium levels, followed by reoxygenation and the concomitant generation of reactive oxygen species during reperfusion (Piper H M, et al., Annals of Thoracic Surgery 2003, 75:644; Yellon D M, et al., New England Journal of Medicine 2007, 357:1121). Reperfusion injury may be responsible for as much as 50% of the damage to the heart following a myocardial infarction (Yelton D M, et al., New England Journal of Medicine 2007, 357:1121). Pathological changes can be observed from animal trials and clinic trials, such as myocytes swelling, damages of plasma membranes, ultrastructural ruptured myofibers, small capillaries damages and more ischemia. Therefore IRI exerts an important influence on the restoration of cardiac structure and function after myocardial ischemia reperfusion.

With the development of medical science recently, IRI has drawn an increasingly number of attention. Numerous treatments may cause IRI including replantation of a severed limb, organ transplantation, coronary artery bypass surgery, thrombolytic therapy and shock treatment.

The mechanism of IRI is still not clear, and the possible mechanism may contain the following: reactive oxygen species induce cell damage (Bhogal R H et al., Liver Transpl, 2010, 16(11): 1303-1313), calcium ions uptake (Shen A C., Am J Pathol, 1979, 67(3): 441-452; Sjaastad I., Acta Physiol Scand, 2002, 175(4): 261-269), energy metabolism obstacle (Gu T X, et al., Chinese Journal of Cardiology, 2001, 29(7): 420-423; Nordlie M A., J Cardiovase Pharmacol Ther, 2006, 11(1): 17-30), the aggregation of neutrophilic granulocytes (Hoffman J W., J Extra Corpor Technol, 2004, 36(4): 391-411). The optional treatments to preventing IRI are restoring blood flow as soon as possible to shorten the ischemia time, therapeutic hypothermia, scavenging free radical by free radical scavengers such as exogenous SOD, allopurinol, Vitamin E, Vitamin C, catalase, dimethyl sulfoxide (DMSO) and so on; improving the ischemic tissue metabolism, for example, adding glycolysis substrate-hexosephosphate, exogenous ATP, hydroquinone, cytochrome C, immunosuppressants, such as cyclosporin A, tacrolimus, mycophenolate mofetil, monoclonal antibodies such as basiliximab, daclizumab and muromonab, corticosteroids and so on. Although optional treatments are available, disappointing clinical outcomes have been yielded. Thus there is a significant need for new and more effective therapies and therapeutic agents for preventing, treating and delaying ischemia reperfusion injury resulting various ischemic conditions.

Neuregulin (NRG; heregulin, HRG), belongs to EGF-like family, which is a family of structurally related growth and differentiation factors that include NRG1, NRG2, NRG3 and NRG4 and iso forms thereof. It is reported that neuregulin performs a series of biological functions, such as stimulating breast cancer cell differentiation and milk protein secretion (Lessor T. J Cell Biochem. 1998; 70(4):587-595), induction of the differentiation of neural crest cell into Schwann cell (Topilko P. Mol Cell Neurosci. 1996; 8(2-3):71-75), stimulating acetylcholine receptor synthesis in skeletal muscle cells (Altiok N. EMBO J. 1995:14(17):4258-4266) and improving cardiocyte differentiation, survival and DNA synthesis (Zhao Y Y. J Biol Chem. 1998; 273(17):10261-10269). It has been demonstrated that neuregulin is essential for the development of heart and nervous system in nrg deficient mice.

NRGs bind to the EGF receptor family, which comprises EGFR, ErbB2, ErbB3 and ErbB4, each of which plays an important role in multiple cellular functions, including cell growth, differentiation and survival. They are protein tyrosine kinase receptors, consisting of an extracellular ligand-binding domain, transmembrane domain and cytoplasmic tyrosine kinase domain. After NRG binds to the extracellular domain of ErbB3 or ErbB4, it induces a conformational change that leads to heterodimer formation between ErbB3, ErbB4 or ErbB2 or homodimer formation between ErbB4 itself, which results in phosphorylation of the receptor'C-terminal domain inside the cell membrane. The phosphorylated intracellular domain then binds additional signal protein inside the cell, activating the corresponding downstream AKT or ERK signaling pathway, and inducing a series of cell reactions, such as stimulation or depression of cell proliferation, cell differentiation, cell apoptosis, cell migration or cell adhesion. Among these receptors, mainly ErbB2 and ErbB4 are expressed in the heart (Zhao Y Y. Etc, Circ Res. 1999; 84(12):1380-1387).

It has been shown that the EGF-like domain of NRG1, ranging in size from 50 to 64 amino acids, are sufficient to bind to and activate these receptors (Culouscou J M, et al., J Biol Chem. 1995; 270(21):12857-12863). Previous studies have shown that neuregulin-1β (NRG-1β) can bind directly to ErbB3 and ErbB4 with high affinity. The orphan receptor, ErbB2, can form a heterodimer to ErbB3 and ErbB4 with higher affinity than ErbB3 or ErbB4 homodimers. Research in neural development has indicated that the formation of the sympathetic nervous system requires an intact NRG-1β, ErbB2 and ErbB3 signaling system (Britsch S. etc, Genes Dev. 1998; 12(12):1825-1836). Targeted disruption of the NRG-1β or ErbB2 or ErbB4 led to embryonic lethality due to cardiac development defects (Gassmann M. etc, Nature. 1995; 378(6555):390-394). Recent studies also highlighted the roles of NRG-1β, ErbB2 and ErbB4 in the cardiovascular development as well as in the maintenance of adult normal heart function (Kuramochi Y. etc, J Mol Cell Cardiol. 2006; 41(2):228-235). NRG-1β has been shown to enhance sarcomere organization in adult cardiomyocytes. The short-term administration of a recombinant NRG-1β EGF-like domain significantly improves or protects against deterioration in myocardial performance in several distinct animal models of heart failure (Liu et al. J Am Coll Cardiol. 2006; 48: 1438-1447). In clinic trial NRG is used to treat heart failure originated from various kinds of cardiac diseases and it is shown to improve cardiac function (published as WO2010/142141). The animal model of middle cerebral artery occlusion reperfusion shows that NRG-1 plays an important role in protecting cerebral cells as it inhibit cerebral cells apoptosis, strengthen the function of nervous system and reduce the infarction size (Li Q., Neurosci Lett. 2008; 443(3):155-159). It is proved that cardiac ischemia-reperfusion induces NRG-1 release and activates NRG/ErbB signaling pathway in cardiac myocytes (Kuramochi Y., J Biol Chem. 2004; 279(49):51141-51147), but the function of NRG-1 in the cardiac ischemia-reperfusion injury is unknown.

The present invention provides methods and compositions for preventing, treating and/or delaying ischemia reperfusion injury.

THE CONTENT OF THE INVENTION

A. Summary of the Invention

The present invention is based on the discovery that NRG is essential to cardiovascular development as well as the maintenance of adult normal heart function. And it enhances cardiac muscle cell differentiation and organization of sarcomeric and cytoskeleton structure, as well as cell adhesion. The present invention is also based on the discovery that NRG significantly improves or protects against deterioration in myocardial performance in distinct animal models of heart failure and prolongs survival of heart failure animals as well as protects cerebral cells in the animal model of middle cerebral artery occlusion reperfusion. Neuregulin, neuregulin polypeptide, neuregulin derivatives, or compounds which mimic the activities of neuregulins, fall within the scope of the present invention.

In a first aspect of the invention, a pharmaceutical composition is provided for preventing, treating or delaying the ischemia-reperfusion injury in mammals, particularly in humans. In a preferred embodiment of the invention, the ischemia reperfusion injury is myocardial ischemia reperfusion injury. The composition comprises an effective amount of the neuregulin protein, or a functional fragment thereof, or a nucleic acid encoding the neuregulin protein, or a functional fragment thereof, or an agent that enhances production and/or function of said neuregulin.

In a second aspect of the invention, a method is provided for preventing, treating or delaying the ischemia-reperfusion injury in mammals, particularly in humans. In a preferred embodiment of the invention, the ischemia reperfusion injury is myocardial ischemia reperfusion injury. The method comprises administrating to a mammal particularly a human having or would have the ischemia-reperfusion injury, to which such prevention, treatment or delay is needed or desirable, an effective amount of the neuregulin protein, or a functional fragment thereof, or a nucleic acid encoding the neuregulin protein, or a functional fragment thereof, or an agent that enhances production and/or function of said neuregulin, whereby said ischemia-reperfusion injury is prevented, treated or delayed.

In a third aspect of the invention, a combination is provided for preventing, treating or delaying the ischemia-reperfusion injury in mammals, particularly in humans. The combination comprises the pharmaceutical composition described above which comprises an effective amount of the neuregulin protein, or a functional fragment thereof, or a nucleic acid encoding the neuregulin protein, or a functional fragment thereof, or an agent that enhances production and/or function of said neuregulin and other prophylactic or therapeutic drugs which can be used for preventing, treating or delaying the cardiac ischemia-reperfusion injury. In a preferred embodiment of the invention, the ischemia reperfusion injury is myocardial ischemia reperfusion injury.

In a forth aspect of the invention, a kit is provided for preventing, treating or delaying the ischemia-reperfusion injury in mammals, particularly in humans, the kit comprises one dose of or several doses of pharmaceutical preparation or composition mentioned above for preventing, treating or delaying the ischemia-reperfusion injury in mammals, particularly in humans. In a preferred embodiment of the invention, the ischemia reperfusion injury is myocardial ischemia reperfusion injury.

The pharmaceutical preparation or composition in the present invention can be used before, during or after the ischemia-reperfusion injury. As being used for prevention, the pharmaceutical preparation or composition can be used in advance and for treatment generally after the injury. In a certain embodiment the pharmaceutical preparation or composition was used before the myocardial ischemia. In a certain embodiment, it was used after the myocardial ischemia but before reperfusion. In another embodiment, it was used after the ischemia-reperfusion.

B. Definitions

Unless defined otherwise, all technical and scientific terms used herein have the same meaning as are commonly understood by one of ordinary skill in the field to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an" and "the" mean "at least one" or "one or more" unless the context clearly dictates otherwise.

As used herein, "neuregulin" or "NRG" used in the present invention refers to proteins or peptides that can bind and activate ErbB2, ErbB3, ErbB4 or combinations thereof, including but not limited to all neuregulin isoforms, neuregulin EGF domain alone, polypeptide comprising neuregulin EGF-like domain, neuregulin mutants or derivatives, and any kind of neuregulin-like gene products that also activate the above receptors as described in detail below. Neuregulin also includes NRG-1, NRG-2, NRG-3 and NRG-4 proteins, peptides, fragments and compounds that mimic the activities of neuregulin. In preferred embodiments, neuregulin used in the present invention binds to and activates ErbB2/ErbB4 or ErbB2/ErbB3 heterodimers, for example, but not for the purpose of restriction, peptide including the 177-237 residues of NRG-1β2 isoform containing the amino acid sequence: SHLVK-CAEKEKTFCVNGGECFMVKDLSNPSRYLCKCP-NEFTGDRCQNYVMA SFYKAEELYQ (SEQ ID NO:1).

Neuregulin used in the present invention can activate the above ErbB receptors and modulate their biological reactions, e.g., stimulating acetylcholine receptor synthesis in skeletal muscle cells, and/or improving cardiocyte differentiation, survival and DNA synthesis. Neuregulin also includes those variants with conservative amino acid substitutions that do not substantially alter their biological activity. Suitable conservative substitutions of amino acids are known to those of skill in this field and may be made generally without altering the biological activity of the resulting molecule. Those of skill in this field recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224). The neuregulin in the present invention can be available by separation from native source, recombinant DNA technology, artificial synthesis or some other approach.

As used herein, "epidermal growth factor-like domain" or "EGF-like domain" refers to a polypeptide motif encoded by the neuregulin gene that binds to and activates ErbB2, ErbB3, ErbB4 or combinations thereof, and bears a structural similarity to the EGF receptor-binding domain as disclosed in WO 00/64400, Holmes et al., Science, 256: 1205-1210 (1992); U.S. Pat. Nos. 5,530,109 and 5,716,930; Hijazi et al., Int. J. Oncol., 13:1061-1067 (1998); Chang et al., Nature, 387:509-512(1997); Carraway et al., Nature, 387:512-516 (1997); Higashiyama et al., J. Biochem., 122: 675-680 (1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain comprises the amino acid sequence corresponding to amino acid residues 177-226, 177-237 or 170-240 of NRG-1. In certain embodiments, EGF-like domain comprises the amino acid sequence of the receptor binding domain of the NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro, as described in U.S. Pat. No. 5,834,229.

Ischemia reperfusion injury refers to an injury to a cell, tissue or organ when blood supply returns to the cell, tissue or organ after a period of ischemia. Injuries that result from ischemia and reperfusion can affect various tissues and organs. Such injuries may be treated by the compositions and methods of the invention, including, for example, cardiovascular ischemia reperfusion injury, cerebrovascular ischemia reperfusion injury, renal ischemia reperfusion injury, hepatic ischemia reperfusion injury, cutaneous ischemia reperfusion injury, bowel ischemia reperfusion injury, intestinal ischemia reperfusion injury, gastric ischemia reperfusion injury, pulmonary ischemia reperfusion injury, pancreatic ischemia reperfusion injury, skeletal muscle ischemia reperfusion injury, abdominal muscle ischemia reperfusion injury, limb ischemia reperfusion injury, mesenteric ischemia reperfusion injury.

An ischemia reperfusion injury can be caused, for example, by a natural event (e.g., restoration of blood flow following a myocardial infarction), a trauma, or by one or more surgical procedures or other therapeutic interventions that restore blood flow to a cell, tissue, or organ that has been subjected to a diminished supply of blood. Such surgical procedures or therapeutic interventions include, for example, coronary artery bypass graft surgery, coronary angioplasty, organ transplant surgery, limb replantation surgery, thrombolytic therapy, shock treatment, and cardiopulmonary bypass surgery.

For the treatment of ischemia reperfusion injury caused by therapeutic interventions, such as surgical procedures, it is preferable that a composition of the invention is administered to a subject undergoing treatment prior to the therapeutic intervention. For example, a composition of the invention can be administered to a subject undergoing treatment, e.g., about 5 minutes, about 10 minutes, about 20 minutes, about 30 minutes, about 1 hour, about 2 hours, about 3 hours, about 4 hours, about 12 hours, about 24 hours, about 48 hours, about 1 weeks prior to the therapeutic intervention. Alternatively, or in addition, a composition of the invention can be administered to a subject undergoing treatment at the time of, or during, the therapeutic intervention. For example, the composition of the invention can be administered continuously throughout the duration of a therapeutic intervention, or the composition of the invention can be administered one or several times during the course of a therapeutic intervention in intervals (e.g., 15 minute intervals). Furthermore, the composition of the invention can be administered to a subject undergoing treatment after a therapeutic intervention. For example, a composition of the invention can be administered to a subject undergoing treatment, e.g., about 5 minutes, about 15 minutes, about 30 minutes, about 1 hour, about 2 hours, about 3 hours, about 4 hours, about 12 hours, about 24 hours, about 48 hours, about 1 week after the therapeutic intervention.

As used herein, "an effective amount" is an amount sufficient to achieve a desired effect under the conditions of administration, in vitro, in vivo or ex vivo, such as, for example, an amount sufficient to inhibit or treat ischemia reperfusion injury in a subject. The effectiveness of a therapy can be determined by suitable methods known by those of skill in the art. In certain embodiments, an effective amount means an amount of the composition of the inven- tion which is sufficient to reduce the infarction size. In certain embodiments, the effective amount of NRG is from about 0.1 μg/kg to about 1 mg/kg, from about 0.1 μg/kg to about 10 μg/kg, from about 0.3 μg/kg to about 1 μg/kg, from about 10 μg/kg to about 100 μg/kg, from about 5 μg/kg to about 20 μg/kg, from about 10 μg/kg to about 30 μg/kg. In certain embodiments, the effective amount of NRG is from about 2 U/kg to about 20000 U/kg, from about 2 U/kg to about 200 U/kg, from about 6 U/kg to about 20 U/kg, from about 200 U/kg to about 2000 U/kg, from about 100 U/kg to about 400 U/kg, from about 200 U/kg to about 600 U/kg. In certain embodiments, the effective amount of NRG is from about 0.1 μg/kg/day to about 1 g/kg/day, from about 0.1

μg/kg/day to about 10 μg/kg/day, from about 0.3 μg/kg/day to about 1 μg/kg/day, from about 10 μg/kg/day to about 100 μg/kg/day, from about 5 μg/kg/day to about 20 μg/kg/day, from about 10 μg/kg/day to about 30 μg/kg/day. In certain embodiments, the effective amount of NRG is from about 2 U/kg/day to about 20000 U/kg/day, from about 2 U/kg/day to about 200 U/kg/day, from about 6 U/kg/day to about 20 U/kg/day, from about 200 U/kg/day to about 2000 U/kg/day, from about 100 U/kg/day to about 400 U/kg/day, from about 200 U/kg/day to about 600 U/kg/day.

As used herein, "activity unit" or "1U" means the quantity of standard product that can induce 50% maximal reaction. In other words, to determine the activity unit for a given active agent, the EC50 must be measured. For example, if the EC50 for a batch of product was 0.05 μg/ml then that would be one unit. Further, if 1 μg of that product is being used then 20U (1/0.05) is being used. The EC50 can be determined by any method known in the art, including the method employed by the inventors in the Examples below. This determination of the activity unit is important for quality control of genetically engineered products and clinically used drugs, permits product from different pharmaceuticals and/or different batch numbers to be quantified with uniform criteria.

In certain embodiments, unit of neuregulin is determined by measuring the activity of neuregulin through kinase receptor activation enzyme-linked immunosorbant assay (KIRA-ELISA) as described in detail in WO03/099300, and Sadick et al., 1996, Analytical Biochemistry, 235:207-14, the contents of which are incorporated by reference in their entireties. Briefly, the assay measures neuregulin induced ErbB2 activation and phosphorylation on the adherent breast carcinoma cell line, MCF-7. Membrane proteins are solubilized via Triton X-100 lysis and the receptor is captured in ELISA wells coated with ErbB2-specific antibodies (e.g., H4) with no cross-reaction to ErbB3 or ErbB4. The degree of receptor phosphorylation is then quantified by antiphosphotyrosine ELISA.

The composition of the invention can be administered, for example, by intravenous infusion, orally, intraperitoneally, or subcutaneously. Intravenous administration is the preferred method of administration. In certain embodiments, the composition of the invention is administered to a subject by continuous infusion for at least 1 hour per day, for at least 4 hours per day, for at least 10 hours per day, for at least 12 hours per day, for at least 18 hours per day, or for at least 24 hours per day.

The composition of the invention can also be administered to the subject in a dosing schedule or "therapeutic cycle". Daily dosage and schedule of the composition is described in detail above. The therapeutic cycle can last 2 days, 5 days, 7 days, 10 days, 2 weeks, 3 weeks, 4 weeks, 2 months, 3 months or 6 months.

The formulations of the composition can be presented in single-dose or multi-dose sealed containers, such as ampoules and vials.

The composition of the invention can be used to prevent, treat, and/or delay ischemia reperfusion injury in combination with other drugs used for preventing, treating and/or delaying the ischemia-reperfusion injury. These drug, including but not limited to, free radical scavengers such as exogenous SOD, allopurinol, Vitamin E, Vitamin C, catalase, dimethyl sulfoxide (DMSO), drugs that can improve the metabolism of ischemic tissues, such as glycolysis substrate-hexosephosphate, exogenous ATP, hydroquinone, cytochrome C and immunosuppressants, such as cyclosporin A, tacrolimus, mycophenolate mofetil, monoclonal antibodies such as basiliximab, daclizumab and muromonab, corticosteroids and so on. The composition of the invention can be administered concurrently with the other drugs, prior to the administration of the other drugs, or after the administration of the other drugs, when administered in combination for preventing, treating, and/or delaying ischemia reperfusion injury.

BRIEF DESCRIPTION OF THE DRAWING

FIG. 1: The results of TCC staining on the sections of rat heart. White district in section (TCC unstaining) is the infarction district. Letter "A", "B", "C" and "D" represents Group A, Group B, Group C and Group D respectively.

EXAMPLES

The invention will be further illustrated by reference to the following non-limiting examples. The examples are put forth so as to provide those of ordinary skill in the art with a complete disclosure and description of how to make and use the present invention, and are not intended to represent that the experiments below are all or the only experiments performed.

Example 1: Therapeutic Effect of Recombinant Human Neuregulin-1 on Myocardial Ischemia Reperfusion in Rat Testing Drug and Reagents:
rhNRG-1: produced by Zensun (Shanghai) Science & Technology Ltd, having the amino acids of SEQ ID NO:1, batch number: 200503007; each vial contains 250 μg (5000U) rhNRG-1.

Placebo: vehicle of rhNRG-1, produced by Zensun (Shanghai) Science & Technology Co Ltd, batch number: 200503001F.

rhThymosin-β4: produced by Northland (Beijing) Bio-Technology Co Ltd, batch number: 20050728.

Wistar rats (male, 200~240 g) were divided into groups and administered with different dosages of rhNRG-1, placebo or rhThymosin-β4 (as shown in Table 1) after anaesthetized with intra-abdominal injection of 20% urethane (5 ml/kg). Thirty minutes after the drug started to be given to the rats, the anterior descending limb of the left coronary artery was ligated for 45 minutes to cause partial myocardium turned white obviously in the ligation area. After that the ligation thread was loosen to keep coronary blood flow for 2 hours and then take out the heart rapidly and wash vascular fat away with normal saline, and then freeze the heart in −30° C. for one hour.

Cut the heart parallelly from apex to base along coronary sulcus to myocardium sections with the thickness of 1 mm, and then put them into TCC dye liquor for 20 min in 37° C. in a shaker. After staining extra dye was washed immediately with water, and then the sections were put into 4% formalin for one hour. Photo and analyze the total size and the infarction size of were analyzed with Image Analysis Software. Infarction size ratio equals to the ratio of the infarction size and the total size of the myocardium section.

Results show that the infarction size ratio of Group A (Placebo Group) is 0.178±0.047 while Group B (I0μg/kg/h rhNRG-1) is 0.130±0.049, and the infarction size of Group B was significantly smaller than that of Group A (P<0.05). The data of Group C is 0.121±0.047 and the size was significantly smaller than that of Group A (P<0.05). The data of Group D is 0.151±0.030 and there was no significant difference with other groups. (Details can be seen in Table 2 and FIG. 1).

TABLE 1

The groups of the experiment

| | Drug | Dosage | Method |
|---|---|---|---|
| Group A | Placebo | 10 µg/kg/h | Continuously infusion through tail vein till the end |
| Group B | rhNRG-1 | 10 µg/kg/h | Continuously infusion through tail vein till the end |
| Group C | rhNRG-1 | 30 µg/kg/h | Continuously infusion through tail vein till the end |
| Group D | rhThymosin-β4 | 2.5 mg/kg | Single intraperitoneal injection |

TABLE 2

The effect of rhNRG-1 to the myocardial infarction size after ischemia reperfusion

| Group | Drug | The number of rat | The myocardium infarction size ratio |
|---|---|---|---|
| Group A | Vehicle | 9 | 0.178 ± 0.047 |
| Group B | rhNRG-1 | 20 | 0.130 ± 0.049* |
| Group C | rhNRG-1 | 11 | 0.121 ± 0.047* |
| Group D | rhThymosin-β4 | 9 | 0.151 ± 0.030 |

What is claimed is:

1. A method of treating or delaying myocardial ischemia reperfusion injury caused by coronary artery bypass graft surgery, coronary angioplasty, or cardiopulmonary bypass surgery in a mammal, comprising administering to the mammal in need thereof, via continuous intravenous infusion, an effective amount of neuregulin (NRG) protein or a functional fragment thereof after the artery bypass graft surgery, coronary angioplasty, or cardiopulmonary bypass surgery, wherein the myocardial ischemia reperfusion injury caused by coronary artery bypass graft surgery, coronary angioplasty, or cardiopulmonary bypass surgery is treated or delayed, wherein the effective amount is a dosage of 10 to 30 µg/kg/h.

2. The method of claim 1, wherein the NRG protein is NRG-1, NRG-2, NRG-3 or NRG-4 protein.

3. The method of claim 1, wherein the NRG protein is NRG-1 protein.

4. The method of claim 1, wherein the NRG protein or a functional fragment thereof comprises the epidermal growth factor (EGF)-like domain of NRG-1.

5. The method of claim 1, wherein the NRG protein or a functional fragment thereof comprises amino acids set forth in SEQ ID NO: 1.

6. The method of claim 1, further comprising administering to the mammal a prophylactic or therapeutic agent for ischemia reperfusion injury.

7. The method of claim 6, wherein said prophylactic or therapeutic agent is selected from the group consisting of a free radical scavenger, an immunosuppressant and an agent which improves the metabolism of ischemic tissue.

8. The method of claim 7, wherein said free radical scavenger are selected from the group consisting of exogenous superoxide dismutase (SOD), allopurinol, Vitamin E, Vitamin C, catalase, and dimethyl sulfoxide (DMSO).

9. The method of claim 7, wherein said immunosuppressant is selected from the group consisting of cyclosporin A, tacrolimus, mycophenolate mofetil, a monoclonal antibody and a corticosteroid.

10. The method of claim 9, wherein said monoclonal antibody is selected from the group consisting of basiliximab, daclizumab, and muromonab.

11. The method of claim 7, wherein said agent which improves the metabolism of ischemic tissue is selected from a group consisting of glycolysis substrate-hexosephosphate, exogenous ATP, hydroquinone, and cytochrome C.

12. The method of claim 1, wherein the mammal is a human.

13. A method of treating or delaying myocardial ischemia reperfusion injury caused by coronary artery bypass graft surgery, coronary angioplasty, or cardiopulmonary bypass surgery in a mammal, comprising (i) performing coronary artery bypass graft surgery, coronary angioplasty, or cardiopulmonary bypass surgery in the mammal, and (ii) after step (i) administering to the mammal, via continuous intravenous infusion, an effective amount of neuregulin (NRG) protein or a functional fragment thereof, wherein the effective amount is a dosage of 10 to 30 µg/kg/h.

14. The method of claim 13, wherein the NRG protein is NRG-1, NRG-2, NRG-3 or NRG-4 protein.

15. The method of claim 13, wherein the NRG protein is NRG-1 protein.

16. The method of claim 13, wherein the NRG protein or a functional fragment thereof comprises the epidermal growth factor (EGF)-like domain of NRG-1.

17. The method of claim 13, wherein the NRG protein or a functional fragment thereof comprises amino acids set forth in SEQ ID NO: 1.

18. The method of claim 13, further comprising administering to the mammal a prophylactic or therapeutic agent for ischemia reperfusion injury.

19. The method of claim 18, wherein said prophylactic or therapeutic agent is selected from the group consisting of a free radical scavenger, an immunosuppressant and an agent which improves the metabolism of ischemic tissue.

20. The method of claim 19, wherein said free radical scavenger are selected from the group consisting of exogenous superoxide dismutase (SOD), allopurinol, Vitamin E, Vitamin C, catalase, and dimethyl sulfoxide (DMSO).

* * * * *

SEQUENCE LISTING

<160> NUMBER OF SEQ ID NOS: 1

<210> SEQ ID NO 1
<211> LENGTH: 61
<212> TYPE: PRT
<213> ORGANISM: Homo sapiens

<400> SEQUENCE: 1

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60